United States Patent
Ohchi

(10) Patent No.: US 7,361,421 B2
(45) Date of Patent: Apr. 22, 2008

(54) LUBRICANT, MAGNETIC RECORDING MEDIUM AND PRODUCTION METHOD OF MAGNETIC RECORDING MEDIUM

(75) Inventor: Yukikazu Ohchi, Kadoma (JP)

(73) Assignee: Matsushita Electric Industrial Co., Ltd., Osaka (JP)

( * ) Notice: Subject to any disclaimer, the term of this patent is extended or adjusted under 35 U.S.C. 154(b) by 245 days.

(21) Appl. No.: 11/126,153

(22) Filed: May 11, 2005

(65) Prior Publication Data

US 2005/0255338 A1 Nov. 17, 2005

(30) Foreign Application Priority Data

May 12, 2004 (JP) ............................ P2004-141960
Feb. 23, 2005 (JP) ............................ P2005-047435

(51) Int. Cl.
*G11B 5/716* (2006.01)

(52) U.S. Cl. .................................. 428/835.7; 528/271

(58) Field of Classification Search ............. 428/835.8, 428/841, 835.7, 841.2, 841.3; 528/271
See application file for complete search history.

(56) References Cited

U.S. PATENT DOCUMENTS

| | | | | |
|---|---|---|---|---|
| 5,091,249 A | * | 2/1992 | Nishikawa et al. | 428/336 |
| 5,098,883 A | * | 3/1992 | Aono | 503/227 |
| 5,328,737 A | * | 7/1994 | Takahashi et al. | 427/569 |
| 5,364,690 A | * | 11/1994 | Takahashi et al. | 428/212 |
| 5,510,513 A | * | 4/1996 | Kai et al. | 560/197 |
| 5,576,075 A | * | 11/1996 | Kawasaki et al. | 427/565 |
| 5,604,032 A | * | 2/1997 | Kai et al. | 428/336 |
| 5,637,390 A | * | 6/1997 | Isobe et al. | 428/323 |
| 5,637,393 A | * | 6/1997 | Ueda et al. | 428/332 |
| 5,712,028 A | * | 1/1998 | Seki et al. | 428/216 |
| 5,776,602 A | * | 7/1998 | Ueda et al. | 428/332 |
| 5,798,135 A | * | 8/1998 | Ueda et al. | 427/130 |
| 5,837,357 A | * | 11/1998 | Matsuo et al. | 428/212 |
| 5,855,746 A | * | 1/1999 | Prabhakara et al. | 204/192.16 |
| 5,869,186 A | * | 2/1999 | Usuki et al. | 428/421 |
| 5,958,542 A | * | 9/1999 | Ootake et al. | 428/833.5 |
| 6,096,445 A | * | 8/2000 | Terakado et al. | 428/848.3 |
| 6,136,403 A | * | 10/2000 | Prabhakara et al. | 428/833.5 |

(Continued)

FOREIGN PATENT DOCUMENTS

EP 0 643 125 3/1995

(Continued)

*Primary Examiner*—Holly Rickman
*Assistant Examiner*—Gary Harris
(74) *Attorney, Agent, or Firm*—Wenderoth, Lind & Ponack, L.L.P.

(57) ABSTRACT

A lubricant is obtained by mixing at least one compound selected from specific fluorine-based diester dicarboxylic acid compounds having has two carboxyl groups, two ester bonds, terminal groups each of which is an alkyl group or an alkenyl group, and one fluoroether or one fluoropolyether chain with at least one compound selected from specific fluorine-based diester compounds having two ester bonds, two terminal groups each of which is an alkyl group or an alkenyl group, one fluoroether or one fluoropolyether chain and specific fluorine-based monoester compounds one ester bond, one terminal group that is an alkyl group or an alkenyl group, and one terminal group that is a fluoroalkyl group, a fluoroether group or a fluoropolyether group, and preferably a specific fluorine-based amino-alcohol compound, and this lubricant is used to form a lubricant layer of a magnetic recording medium.

11 Claims, 1 Drawing Sheet

U.S. PATENT DOCUMENTS

| | | | |
|---|---|---|---|
| 6,136,421 A * | 10/2000 | Chen | 428/216 |
| 6,177,150 B1 * | 1/2001 | Fujita et al. | 427/586 |
| 6,194,047 B1 * | 2/2001 | Hayashi | 428/848.1 |
| 6,245,417 B1 * | 6/2001 | Huang | 428/216 |
| 6,258,434 B1 * | 7/2001 | Hayashi | 428/835 |
| 6,268,073 B1 * | 7/2001 | Chen | 428/825.1 |
| 6,303,214 B1 * | 10/2001 | Chour et al. | 428/212 |
| 6,303,227 B1 * | 10/2001 | Kuwahara et al. | 428/421 |
| 6,324,131 B1 * | 11/2001 | Chen | 369/13.4 |
| 6,355,342 B1 * | 3/2002 | Chen | 428/332 |
| 6,381,200 B1 * | 4/2002 | Chen | 369/13.38 |
| 6,537,668 B1 * | 3/2003 | Vijayen et al. | 428/408 |
| 6,544,627 B1 * | 4/2003 | Vijayen et al. | 428/141 |
| 6,565,718 B1 * | 5/2003 | Chour et al. | 204/192.15 |
| 6,565,719 B1 * | 5/2003 | Lairson et al. | 204/192.16 |
| 6,613,422 B1 * | 9/2003 | Ma et al. | 428/212 |
| 6,682,807 B2 * | 1/2004 | Lairson et al. | 428/833.2 |
| 6,696,183 B2 * | 2/2004 | Onodera et al. | 428/837 |
| 6,740,384 B2 * | 5/2004 | Veerasamy et al. | 428/835 |
| 6,748,959 B1 * | 6/2004 | Kashiwaya et al. | 134/1.1 |
| 6,784,237 B2 * | 8/2004 | Thompson et al. | 524/462 |
| 6,805,891 B2 * | 10/2004 | Vijayen et al. | 428/835 |
| 6,805,941 B1 * | 10/2004 | Hayashi | 428/835 |
| 6,855,232 B2 * | 2/2005 | Jairson et al. | 204/192.16 |
| 6,902,773 B1 * | 6/2005 | Pocker et al. | 427/523 |
| 6,989,356 B2 * | 1/2006 | Kobayashi et al. | 508/477 |
| 6,994,895 B2 * | 2/2006 | Hattori et al. | 427/599 |
| 7,018,729 B2 * | 3/2006 | Pocker et al. | 428/835 |
| 7,081,277 B1 * | 7/2006 | Watanabe et al. | 427/493 |
| 7,083,873 B2 * | 8/2006 | Hayashi | 428/835 |
| 7,125,827 B2 * | 10/2006 | Li et al. | 508/389 |
| 7,144,606 B2 * | 12/2006 | Huang | 427/535 |
| 2002/0128412 A1 * | 9/2002 | Kitahara et al. | 526/250 |
| 2002/0168550 A1 * | 11/2002 | Onodera et al. | 428/694 TM |
| 2004/0005458 A1 * | 1/2004 | Hattori et al. | 428/402 |
| 2005/0155214 A1 * | 7/2005 | Hattori et al. | 29/603.15 |

FOREIGN PATENT DOCUMENTS

| | | |
|---|---|---|
| JP | 5-194970 | 8/1993 |
| JP | 2002-92858 | 3/2002 |
| JP | 2002-150530 | 5/2002 |
| JP | 2002-241349 | 8/2002 |
| JP | 2004039102 A * | 2/2004 |

* cited by examiner

LUBRICANT, MAGNETIC RECORDING MEDIUM AND PRODUCTION METHOD OF MAGNETIC RECORDING MEDIUM

TECHNICAL FIELD

This invention is related to a lubricant used for a precision instrument and a precision part which require a precise lubricity, and a magnetic recording medium wherein the lubricant is used and a production method of the magnetic recording medium.

BACKGROUND OF THE INVENTION

Recently, in the field of magnetic recording, with the improvement in performance of recording and reproducing equipment such as digitalization, scale reduction, and elongation of time for use, a high-density magnetic recording medium suitable therefor has been developed actively. Recently, a metal thin film type magnetic recording medium, which is extremely advantageous for a short wavelength recording, is put into practical use in lieu of an application type magnetic recording medium. The metal thin film type magnetic recording medium is generally referred to a tape or a disk, wherein a magnetic layer of a ferromagnetic metal thin film is formed as a recording layer on a non-magnetic base (or a non-magnetic support). Systems for recording information on and reproducing information from the high-density magnetic recording medium include a digital video deck and a hard disk drive.

The magnetic layer of the metal thin film type magnetic recording medium such as a digital video tape has an extremely good surface property, i.e. a small roughness on the surface. For this reason, a contact area between the magnetic layer and a magnetic head is larger, whereby the magnetic layer is liable to be abraded by receiving a great friction force while being in a rapid sliding movement with the magnetic head during a process of recording/reproducing signals. Abrasion of the magnetic layer greatly affects the running durability, the still durability, or the like, so that reduction of the abrasion of the magnetic layer is an important object in the research and development of the metal thin film type magnetic recording medium.

In this situation, an attempt is made to reduce the abrasion by disposing a protective film and a lubricant layer on a surface of the magnetic layer in this order to improve the running durability and the still durability. In the case where the lubricant layer is disposed, the protective film and the lubricant layer on the magnetic layer surface are required to be thin in order to prevent the output reduction caused by a spacing loss between the magnetic recording medium and the magnetic head as much as possible for achieving a high output. Particularly, the lubricant layer is required to exhibit a lubricating property with a thickness as small as several nanometers.

Further, in a typical hard disk drive, a contact start stop (CSS) mode is employed. The "CSS" mode refers to a mode wherein a magnetic head contacts with the disk when a hard disk that is a high-density magnetic recording medium stops, and the magnetic head is floated by an air stream which is caused by a rapid rotation of the hard disk when the drive starts, and recordation and reproduction of information is carried out with the floated magnetic head. When the drive stops, the rotation speed of the disk is reduced and the magnetic head contacts with the hard disk again.

In this CSS mode, the magnetic head runs scrubbing the surface of the hard disk at the time of starting and stopping, which causes friction force that may give a serious problem. It is required that the friction coefficient of the recording medium which has been subjected to a CSS running test is the same as the initial friction coefficient in order to maintain reliability of the hard disk drive. However, it is difficult to meet this requirement for the magnetic disk wherein a surface flatness is high, that is, roughness is small. Further, a problem of "head crash" should be resolved. The "head crash" is collision between the head and the medium during the high speed rotation of the hard disk. One factor of the head clash is that the magnetic recording medium does not have appropriate protective film and lubricant layer.

In this situation, use of lubricants suitable for a magnetic recording medium is widely studied. One of the lubricants is a fluorine-based compound. Since the fluorine-based compound exhibits an excellent lubricating property, use of various compounds is proposed (see Japanese Kokai (Laid-Open) Publication Nos. 2002-92858, 2002-150530(A), 2002-241349(A) and 5-194970/1993(A).

However, the lubricating property of the lubricant used for the magnetic recording medium is required to be further improved in order to adapt to new technologies such as an MR head or a GMR head and a contact recording mode, which technologies are entailed by a higher recording density.

The property which is required for a lubricant used for a magnetic recording medium is: exhibiting superior lubricating property when used under a low-temperature environment; the ability of being applied into a thin film with the lubricating property maintained; maintaining the lubricating property under long-term use; and exhibiting a small powder deposition on a magnetic head. Herein, "powder deposition" means that the lubricant is scraped off during the running of the medium in contact with the magnetic head and the scraped powder deposits on the magnetic head.

These requirements need to be satisfied at a very high level because of the property of the magnetic recording medium. Therefore, the conventional lubricants are difficult to satisfy all these requirements.

In view of the aforementioned situations, the object of the present invention is to provide a lubricant that exhibits excellent lubricity under various use conditions and maintains lubricating effect even if it is subjected to long-time use and gives a magnetic recording medium which exhibits a small powder deposition when the lubricant forms a lubricant layer of the magnetic recording medium, and to provide the magnetic recording medium wherein the lubricant is used and the production method of the magnetic recording medium.

SUMMARY OF THE INVENTION

According to a first aspect of the present invention, a lubricant which has a specific composition is provided. This lubricant includes at least one compound selected from fluorine-based diester dicarboxylic acid compounds represented by a formula (a), and at least one compound selected from fluorine-based diester compounds represented by a formula (b) and fluorine-based monoester compounds represented by a formula (c):

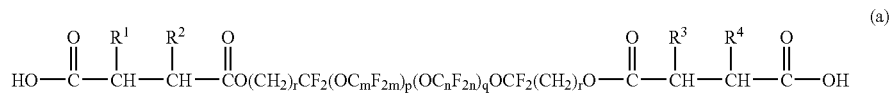
(a)

wherein, $R^1$, $R^2$, $R^3$ and $R^4$ each represent hydrogen, an aliphatic alkyl group or an aliphatic alkenyl group, at least one of $R^1$ and $R^2$ is hydrogen, at least one of $R^3$ and $R^4$ is hydrogen, "m" is an integer of 1 to 6, "n" is an integer of 1 to 5, "p" and "q" each are an integer of 0 to 30 and "r" is an integer of 1 to 12;

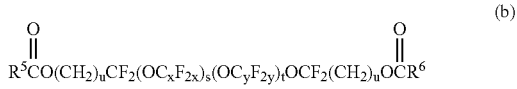
(b)

wherein, $R^5$ and $R^6$ each represent an aliphatic alkyl group or an aliphatic alkenyl group, "x" is an integer of 1 to 6, "y" is an integer of 1 to 5, "s" and "t" each are an integer of 0 to 30 and "u" is an integer of 1 to 12;

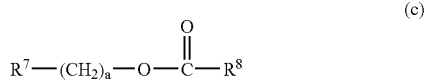
(c)

wherein, $R^7$ represents a fluoroalkyl group, a fluoroalkenyl group, a fluoroether group or a fluoropolyether group, $R^8$ represents an aliphatic alkyl group or an aliphatic alkenyl group, and "a" is an integer of 1 to 12.

The lubricant according to the present invention is characterized in that the compound represented by the formula (a) is combined with the compound represented by the formula (b) and/or the compound represented by the formula (c). When the lubricant including this combination of these specific compounds is used to form a lubricant layer of a magnetic recording medium, the medium exhibits both of excellent running durability and excellent still durability characteristics.

The lubricant according to the present invention may be preferably provided by further combining a compound represented by a formula (d):

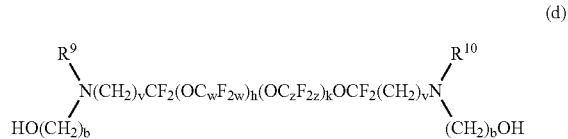
(d)

wherein $R^9$ and $R^{10}$ each represent hydrogen, an aliphatic alkyl group or an aliphatic alkenyl group, "b" is an integer of 1 to 12, "v" is an integer of 1 to 12, "w" is an integer of 1 to 6, "z" is an integer of 1 to 5, and "h" and "k" each are an integer of 0 to 30, with the combination of the compound of the formula (a) and the compound of the formula (b) and/or the compound of the formula (c). The lubricant which further includes the compound represented by the formula (d) can be used to form the lubricating layer of the magnetic recording medium so as to further improve the running durability of the medium.

The reason why a good property is achieved in the magnetic recording medium wherein the lubricant layer is formed of the lubricant of the present invention is considered as follows, but this reason does not limit the present invention. Firstly, in all the compounds represented by the formulae (a) to (c), an ester bond R"COOR has a construction wherein R' of the alkoxyl group has fluorine and R" of an acyl group R"CO— is an aliphatic alkyl group or an aliphatic alkenyl group. That is, the acyl group does not have a fluorine-containing group such as a fluoroalkyl group in the compound contained as main components of the lubricant of the present invention. This contributes to improvement in stability of the lubricant. Further, the compound represented by the formula (a) has carboxyl groups at its terminals, which contributes to improve the running durability of the magnetic recording medium. Each of the compounds represented by the formulae (b) and (c) has an ester bond at its terminal(s), which contributes to increase in the still durability characteristics of the magnetic recording medium and reduces the powder deposition on the magnetic head. Therefore, the combination of at least one compound represented by the formula (a) and at least one compound selected from the compounds represented by the formulae (b) and (c) can achieve good running durability and good still durability and reduced powder deposition in the magnetic recording medium. Furthermore, the compound of the formula (a) and the compound of the formula (b) have a high mutual solubility since the compound of the formula (b) has a fluoroether group in a molecule, similarly to the compound of the formula (a). Therefore, the combination of the compound of the formula (a) and the compound of the formula (b) gives the lubricant which is excellent in uniformity. The compound of the formula (b) can contribute to further improvement in still durability since it includes more ester bonds in one molecule. Although the compound of the formula (c) has fewer ester bonds than the compound of the formula (b), the molecular weight thereof is small and its molecular volume is small, which contributes to improvement in running durability of the magnetic recording medium. Therefore, the combination of the compound of the formula (a) and the compound of the formula (c) can maintain a stable running characteristic of the magnetic recording medium under a low-temperature environment.

The compound represented by the formula (d) has a fluoroalkyl ether as a main chain, and nitrogen atoms at its both ends, each of the nitrogen atoms bonding to one hydroxyalkyl group and bonding to any one of hydrogen, an aliphatic alkyl group and an aliphatic alkenyl group. In the compound represented by the formula (d), the hydroxyalkyl groups bonded to both nitrogen atoms are considered to serve to improve the adhesion of the lubricant to an object (for example, the protective film of the magnetic recording medium). The compound of the formula (d) is characterized in that one hydroxyalkyl group is bonded to each nitrogen atom and the number of hydroxyalkyl groups is limited to two in one molecule. This feature can prevent the excessive adsorption of the compound of the formula (d) to a counter part (for example, the magnetic head of the magnetic recording/reproducing apparatus) which contacts with and slides on the object to which the lubricant is applied, resulting in suppression of deterioration of the lubricating property of the object. Further, this feature prevents the lubricant adsorbed on the counter part (for example, the magnetic head) from coagulating to form powder. Furthermore, in the case where the aliphatic alkyl group or the aliphatic alkenyl group is bonded to at least one of nitrogen atoms, these groups are considered to contribute to improvement in lubricating property. Therefore, it is considered that this compound functions as a lubricant balancing durability and lubricating property as a whole since this compound has the excellent characteristic given by the groups bonded to the nitrogen atoms in addition to the high adhesion strength given by the nitrogen atoms and the lubricating property given by the fluoroalkyl ether chain.

According to a second aspect of the present invention, a magnetic recording medium is provided which comprises a ferromagnetic metal film formed as a magnetic layer on a non-magnetic base, a protective film formed on the magnetic layer and a lubricant layer formed on the protective film, wherein the lubricant layer includes at least one of the lubricants of the present invention. Since the lubricant layer of the magnetic recording medium according to the present invention includes the lubricant of the present invention, the medium has excellent still durability characteristics and excellent running durability.

According to a third aspect of the present invention, a method for producing the magnetic recording medium of the present invention is provided. The production method of the present invention is characterized by a step of forming the lubricant layer. Therefore, one those skilled in the art may employ conventional steps for producing a magnetic recording medium except for the step of forming the lubricant layer. The step of forming the lubricant layer is characterized in that it includes the step of applying an application solution, which is prepared by dissolving compounds that constitute the lubricant layer (that is, the lubricant) into a mixed organic solvent of a hydrocarbon-based solvent and an alcohol-based solvent, on the protective film. Use of the mixed organic solvent of the hydrocarbon-based solvent and the alcohol-based solvent can form a uniform thin lubricant layer with an extremely small amount of application unevenness. Thus, the production method of the present invention makes it possible to obtain a magnetic recording medium having an excellent lubricity and a high practical reliability.

The lubricant of the present invention is obtained by combining a specific fluorine-based diester dicarboxylic acid compound with a specific fluorine-based diester compound and/or a specific fluorine-based monoester compound and it may preferably include a specific fluorine-based amino-alcohol. This lubricant adheres well to a surface of the object (for example, a surface of a carbon film of a magnetic recording medium) to which the lubricity is to be conferred, and exhibits excellent lubricating property under various environments for long time. Therefore, the lubricant of the present invention is useful as a lubricant for various machines, apparatuses, or parts.

The lubricant of the present invention is especially suitable for forming a lubricant layer of a magnetic recording medium which contacts with and slide on the magnetic head. The magnetic recording medium wherein the lubricant layer is formed of the lubricant of the present invention exhibits excellent runnability and durability. Specifically, the medium shows excellent lubricity under various use conditions, maintains the lubricity after long-time use and presents small powder deposition. The magnetic recording medium of the present invention is particularly suitable for being used in a digital video tape recorder and a hard disk drive.

DETAILED DESCRIPTION OF THE PREFERRED EMBODIMENTS

Figure 1:
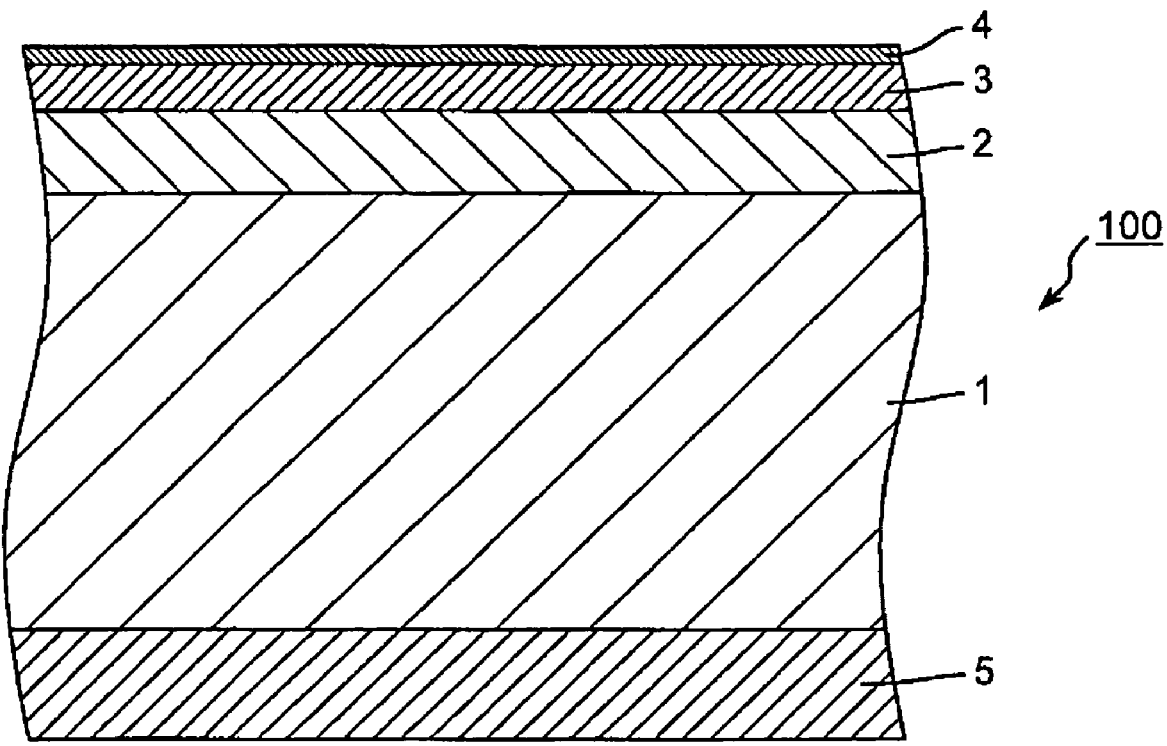
FIG. 1 is a schematic view illustrating a cross section of a magnetic recording medium according to an embodiment of the present invention.

Next, embodiments of the present invention are described below. The lubricant of the present invention contains at least one compound selected form a fluorine-based diester dicarboxylic acid compound represented by the formula (a), and at least one compound selected from a fluorine-based diester compound represented by the formula (b) and a fluorine-based monoester compound represented by the formula (c). It is preferable that the lubricant of the present invention further contain a fluorine-based amino-alcohol. The lubricant of the present invention may optionally contain other components such as another conventional lubricant and a corrosion inhibitor.

The compound represented by the following formula (a) has two carboxyl groups, two ester bonds, terminal groups each of which is an alkyl group or an alkenyl group, and one fluoroether or one fluoropolyether chain.

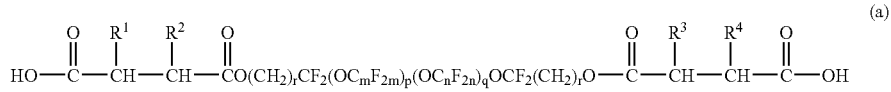

(a)

$$HO-\overset{O}{\underset{\|}{C}}-\overset{R^1}{\underset{|}{CH}}-\overset{R^2}{\underset{|}{CH}}-CO(CH_2)_rCF_2(OC_mF_{2m})_p(OC_nF_{2n})_qOCF_2(CH_2)_rO-\overset{O}{\underset{\|}{C}}-\overset{R^3}{\underset{|}{CH}}-\overset{R^4}{\underset{|}{CH}}-\overset{O}{\underset{\|}{C}}-OH$$

In the formula (a), $R^1$, $R^2$, $R^3$ and $R^4$ each represent hydrogen, an aliphatic alkyl group or an aliphatic alkenyl group, at least one of $R^1$ and $R^2$ is hydrogen, and at least one of $R^3$ and $R^4$ is hydrogen. Therefore, the compounds represented by the formula (a) include:

i) a compound wherein $R^1$ is hydrogen, $R^2$ is the aliphatic alkyl group or the aliphatic alkenyl group, $R^3$ is the aliphatic alkyl group or the aliphatic alkenyl group and $R^4$ is hydrogen;

ii) a compound wherein $R^1$ is the aliphatic alkyl group or the aliphatic alkenyl group, $R^2$ is hydrogen, $R^3$ is hydrogen and $R^4$ is the aliphatic alkyl group or the aliphatic alkenyl group;

iii) a compound wherein $R^1$ is the aliphatic alkyl group or the aliphatic alkenyl group, $R^2$ is hydrogen, $R^3$ is the aliphatic alkyl group or the aliphatic alkenyl group and $R^4$ is hydrogen;

iv) a compound wherein $R^1$ is hydrogen, $R^2$ is the aliphatic alkyl group or the aliphatic alkenyl group, $R^3$ is hydrogen and $R^4$ is the aliphatic alkyl group or the aliphatic alkenyl group; and v) a compound wherein all of $R^1$ to $R^4$ are hydrogen.

In the formula (a), the aliphatic alkyl group or the aliphatic alkenyl group (that is, one or more of $R^1$, $R^2$, $R^3$ and $R^4$ in the case where the one or more of $R^1$, $R^2$, $R^3$ and $R^4$ are the aliphatic alkyl group(s) or the aliphatic alkenyl group(s)) may preferably have 1 to 22 carbon atoms and more preferably 8 to 18 carbon atoms. The aliphatic alkyl group or the aliphatic alkenyl group may be a straight chain or may be branched. In the case where two of $R^1$, $R^2$, $R^3$ and $R^4$ each are the aliphatic alkyl group or the aliphatic alkenyl group, the two groups may be the same group or different from each other.

In the formula (a), "m" is an integer in a range of 1 to 6, "n" is an integer in a range of 1 to 5, "p" is an integer in a range of 0 to 30, and "q" is an integer in a range of 0 to 30. A preferable "m" may be an integer in a range of 2 to 5. A preferable "n" may be an integer in a range of 1 to 4. A preferable combination (m, n) may be (2, 1) or (1, 2). A preferable "p" may be an integer in a range of 2 to 6. A preferable "q" may be an integer in a range of 2 to 6. In the formula (a), "r" is an integer in a range of 1 to 12.

In the formula (a), in the case where a portion represented by $-(OC_mF_{2m})_p(OC_nF_{2n})_q-$ is formed of only one kind of oxyfluoroalkylene, "q" is regarded zero in the formula (a) and the compound of the formula (a) is regarded to include only $(OC_mF_{2m})$ as the oxyfluoroalkylene. In this case, "m" may be preferably two.

In the case where both of "p" and "q" are zero, the compound of the formula (a) includes one ether bond, and therefore includes a fluoroether. In the case of "p"≠0 and "q"=0, or in the case of "p"≧1 and "q"≧1 in the formula (a), the number of ether bonds is two or more, and therefore, the compound contains a fluoropolyether chain.

In the compound of the formula (a), the potion represented by $-(OC_mF_{2m})_p(OC_nF_{2n})_q-$ corresponds to a portion where two kinds of oxyfluoroalkylene units are copolymerized. Herein, "p" and "q" correspond to the numbers of the oxyfluoroalkylene units respectively. The copolymer of $(OC_mF_{2m})$ unit and $(OC_nF_{2n})$ unit may be a block copolymer which consists of a block of "p" units of $(OC_mF_{2m})$ and a block of "q" units of $(OC_nF_{2n})$, or may be another block copolymer, a random copolymer, or an alternating copolymer. Therefore, the formula (a) covers the compound wherein $-(OC_mF_{2m})_p(OC_nF_{2n})_q-$ is the block copolymer, the compound wherein $-(OC_mF_{2m})_p(OC_nF_{2n})_q-$ is the random copolymer and the compound wherein $-(OC_mF_{2m})_p(OC_nF_{2n})_q-$ is the alternating copolymer.

The compound represented by the formula (a) may be produced by mixing a fluoroalkyl-dialcohol having fluoroalkyleneoxide group with an alkyl succinic anhydride, alkenyl succinic anhydride or succinic anhydride, and agitating the mixture under heating. A method for synthesizing the compound of the formula (a) is known as described in Japanese Kokai (Laid-Open) Publication No. 2002-241349 (A) that is incorporated herein by reference, and therefore the detailed explanation thereof is omitted here.

The compound represented by the formula (b) has two ester bonds, two terminal groups each of which is an alkyl group or an alkenyl group, one fluoroether or one fluoropolyether chain in one molecule.

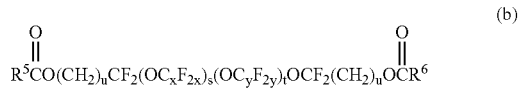

(b)

In the formula (b), the aliphatic alkyl group or the aliphatic alkenyl group (that is, $R^5$ and $R^6$) may preferably have 1 to 30 carbon atoms and more preferably 6 to 20 carbon atoms. When the number of carbon atoms is less than 6, or over 30, the lubricity conferred by the compound may be reduced. The aliphatic alkyl group or the aliphatic alkenyl group may be a straight chain or may be branched.

In the formula (b), "x" is an integer in a range of 1 to 6, "y" is an integer in a range of 1 to 5, "s" is an integer in a range of 0 to 30 and "t" is an integer in a range of 1 to 30. A preferable "x" may be an integer in a range of 2 to 5. A preferable "y" may be an integer in a range of 1 to 4. A preferable combination (x, y) may be (2, 1) or (1, 2). A preferable "s" may be an integer in a range of 2 to 6. A preferable "t" may be an integer in a range of 2 to 6. In the formula (a), "u" is an integer in a range of 1 to 12.

In the case where a portion represented by $-(OC_xF_{2x})_s(OC_yF_{2y})_t-$ is formed of only one kind of oxyfluoroalkylene in the formula (b), "t" is regarded zero and the compound of the formula (b) is regarded to include only $(OC_xF_{2x})$ as the oxyfluoroalkylene. In this case, "x" may be preferably two.

In the case where both of "s" and "t" are zero, the compound of the formula (b) includes one ether bond, and therefore includes a fluoroether. In the case of "s"≠0 and "t"=0, or in the case of "s"≧1 and "t"≧1 in the formula (b), the number of ether bonds is two or more, and therefore, the compound contains a fluoropolyether chain.

In the compound of the formula (b), the potion represented by $-(OC_xF_{2x})_s(OC_yF_{2y})_t-$ corresponds to a portion where two kinds of oxyfluoroalkylene units are copolymerized. Herein, "s" and "t" correspond to the numbers of the oxyfluoroalkylene units respectively. The copolymer of $(OC_xF_{2x})$ unit and $(OC_yF_{2y})$ unit may be a block copolymer which consists of a block of "s" units of $(OC_xF_{2x})$ and a block of "t" units of $(OC_yF_{2y})$, or may be another block copolymer, a random copolymer, or an alternating copolymer. Therefore, the formula (b) covers the compound wherein $-(OC_xF_{2x})_s(OC_yF_{2y})_t-$ is the block copolymer, the compound wherein $-(OC_xF_{2x})_s(OC_yF_{2y})_t-$ is the random copolymer and the compound wherein $-(OC_xF_{2x})_s(OC_yF_{2y})_t-$ is the alternating copolymer.

When the compound of the formula (b) is used as a component of the lubricant of the present invention, the portion represented by $-(OC_mF_{2m})_p(OC_nF_{2n})_q-$ in the formula (a) may be preferably the same as the portion represented by $-(OC_xF_{2x})_s(OC_yF_{2y})_t-$ in the formula (b). In other words, it is preferable that m=x, n=y, p=s, and q=t. In that case, the two components show good mutual solubility since the basic skeletons of two components are common.

A method for synthesizing the compound of the formula (b) may be produced, for example, by reacting a perfluoropolyether having hydroxyl groups at its terminals with a carboxylic acid chloride. The synthesis method of the compound of the formula (b) is known as described in Japanese Kokai (Laid-Open) Publication No. 5-194970/1993(A) that is incorporated herein by reference, and therefore the detailed explanation thereof is omitted here.

The compound represented by the formula (c) has one ester bond, one terminal group that is an alkyl group or an alkenyl group, and one terminal group that is a fluoroalkyl group, a fluoroalkenyl group, a fluoroether group or a fluoropolyether group.

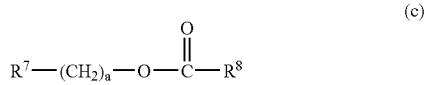

In the formula (c), $R^7$ is a fluoroalkyl group, a fluoroether group, a fluoroalkenyl group or a fluoropolyether group.

In the case where $R^7$ is the fluoroalkyl group or the fluoroalkenyl group, it may preferably have 1 to 12 carbon atoms and more preferably 6 to 10 carbon atoms. The fluoroalkyl group or the fluoroalkenyl group may be a straight chain or may be branched. The fluoroalkyl group or the fluoroalkenyl group may be preferably a perfluoroalkyl group or a perfluoroalkenyl group.

In the case where $R^7$ is the fluoroalkyl group or the fluoroalkenyl group, $R^7$ may have a cyclic fluorinated hydrocarbon group. The cyclic fluorinated hydrocarbon group is a substituent group selected from an aromatic hydrocarbon group wherein a part or all of hydrogen atoms are replaced with fluorine atom(s), an alicyclic hydrocarbon group wherein a part or all of hydrogen atoms are replaced with fluorine atom(s) and a condensed polycyclic hydrocarbon group wherein a part or all of hydrogen atoms are replaced with fluorine atom(s), and it may be preferably the alicyclic hydrocarbon group (that is, a cycloalkyl group). In the cyclic fluorinated hydrocarbon group, all hydrogen atoms may be preferably substituted with fluorine atoms. The cyclic hydrocarbon group substitutes a hydrogen atom or a fluorine atom of the fluoroalkyl group or the fluoroalkenyl group. The cyclic hydrocarbon group may be bonded to any carbon atom of the fluoroalkyl group or the fluoroalkenyl group and it may be bonded as a side chain group. The cyclic hydrocarbon group may be preferably bonded to a terminal carbon of the fluoroalkyl group or the fluoroalkenyl group. The cyclic hydrocarbon group may preferably have 4 to 8 carbon atoms.

In the case where $R^7$ is a fluoroether group or a fluoropolyether group, its molecular weight is preferably in a range of about 200 to about 6000, more preferably in a range of about 300 to about 4000. If the molecular weight is less than 200 or exceeds 6000 and the compound is used for forming a lubricant layer of a magnetic recording medium, the lubricity and the reliability of the medium may decrease. The fluoroether group or the fluoropolyether group may be preferably a perfluoroether group or a perfluoropolyether group.

In the formula (c), $R^8$ is an aliphatic alkyl group or an aliphatic alkenyl group. $R^8$ may preferably have 6 to 30 carbon atoms, and more preferably 10 to 24 carbon atoms. When the number of carbon atoms is less than 6 or exceeds 30, the lubricity may decrease. $R^8$ may be a straight chain or may be branched.

The compound of the formula (c) may be synthesized by reacting a fluorine-containing alcohol with a fatty acid. This reaction may advantageously proceed by mixing and agitating the fluorine-containing alcohol and the fatty acid in a solvent with a catalyst under heating. Heptane, octane, or toluene may be preferably employed as the solvent. Further, when the heating temperature is low, unreacted substances tend to remain in large amounts. When the heating temperature is high, a byproduct tends to be produced. Therefore, the heating temperature may be preferably in a range of 80° C. to 150° C., and more preferably in a range of 120° C. to 130° C. An acid catalyst or a base catalyst may be employed as the catalyst. A preferable acid catalyst may be, for example, p-toluenesulfonic acid. A preferable base catalyst may be pyridine. A fatty acid chloride may be used instead of the fatty acid. In this case, the catalyst may not be used.

In the lubricant of the present invention, the mixing weight ratio of the compound represented by the formula (a) to the compound represented by the formula (b) and/or the compound represented by the formula (c) may be preferably within a range of 1:9 to 9:1, more preferably 2:8 to 9:1 and still more preferably 4:6 to 9:1. When the lubricant contains both of the compounds represented by the formula (b) and the compound represented by the formula (c) (that is, the lubricant is three-component system), the mixing ratio of the former (the formula (b)) to the latter (the formula (c)) may be preferably in a range of 1:9 to 9:1.

The lubricant of present invention may further contain the compound represented by the following formula (d). That is, the lubricant of the present invention may be provided as a three-component system represented by (a)/(b)/(d) or (a)/(c)/(d), or a four-component system represented by (a)/(b)/(c)/(d), wherein (a), (b), (c) and (d) correspond to the compounds represented by the formulae (a), (b), (c) and (d) respectively.

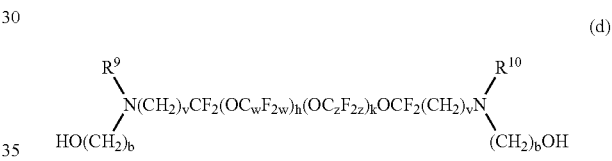

The compound represented by the formula (d) has two nitrogen atoms and two hydroxyalkyl groups and preferably at least one aliphatic alkyl group or aliphatic alkenyl group. It is more preferable that two aliphatic alkyl groups or aliphatic alkenyl groups may be included in the compound of the formula (d).

In the formula (d), $R^9$ and $R^{10}$ each represent hydrogen, an aliphatic alkyl group or an aliphatic alkenyl group, "b" is an integer in a range of 1 to 12, "v" is an integer of 1 to 12, "w" is an integer in a range of 1 to 6, "z" is an integer in a range of 1 to 5, "h" is an integer in a rage of 0 to 30 and "k" is an integer in a range of 0 to 30.

In the formula (d), $R^9$ and $R^{10}$ are generally the same, but they may be different from each other. When $R^9$ and $R^{10}$ are different from each other, one of them may be hydrogen. Alternatively, both of $R^9$ and $R^{10}$ may be hydrogen. Although the compound wherein $R^9=R^{10}=H$ exhibits a little inferior lubricity compared to the compounds wherein $R^9$ and/or $R^{10}$ is the aliphatic alkyl group or the aliphatic alkenyl group, the compound wherein $R^9=R^{10}=H$ ensures an appropriate adsorption by two hydroxyalkyl groups and it may be preferably used as a component of the lubricant of the present invention.

In the formula (d), the aliphatic alkyl group or the aliphatic alkenyl group (that is, $R^9$ and/or $R^{10}$) may preferably have 1 to 30 carbon atoms, and more preferably 6 to 20 carbon atoms. When the number of carbon atoms is less than 6 or exceeds 30, the lubricity conferred by the compound may decrease. The aliphatic alkyl group or the aliphatic alkenyl group may be a straight chain or may be branched.

In the formula (d), "w" is an integer in a range of 1 to 6, "z" is an integer in a range of 1 to 5, "h" is an integer in a range of 0 to 30 and "k" is an integer in a range of 0 to 30. A preferable "w" may be an integer in a range of 2 to 5. A preferable "z" may be an integer in a rage of 1 to 4. A preferable combination (w, z) may be (2, 1) or (1, 2). A preferable "h" may be an integer in a range of 2 to 6. A preferable "k" may be an integer in a range of 2 to 6. In the formula (d), "b" is an integer in a range of 1 to 12, and "v" is an integer in a range of 1 to 12.

In the case where a portion represented by $-(OC_wF_{2w})_h(OC_zF_{2z})_k-$ is formed of only one kind of oxyfluoroalkylene in the formula (d), "k" is regarded zero and the compound of the formula (d) is regarded to include only $(OC_wF_{2w})$ as the oxyfluoroalkylene. In this case, "w" may be preferably two.

In the case where both of "h" and "k" are zero, the compound of the formula (d) includes one ether bond, and therefore includes a fluoroether. In the case of "h"≠0 and "k"=0, or in the case of "h"≧1 and "k"≧1 in the formula (d), the number of ether bonds is two or more, and therefore, the compound contains a fluoropolyether chain.

In the compound of the formula (d), the potion represented by $-(OC_wF_{2w})_h(OC_zF_{2z})_k-$ corresponds to a portion where two kinds of oxyfluoroalkylene units are copolymerized. Herein, "h" and "k" correspond to the numbers of the oxyfluoroalkylene units respectively. The copolymer of $(OC_wF_{2w})$ unit and $(OC_zF_{2z})$ unit may be a block copolymer which is made of a block of "h" units of $(OC_wF_{2w})$ and a block of "k" units of $(OC_zF_{2z})$, or may be another block copolymer, a random copolymer, or an alternating copolymer. Therefore, the formula (d) covers the compound wherein $-(OC_wF_{2w})_h(OC_zF_{2z})_k-$ is the block copolymer, the compound wherein $-(OC_wF_{2w})_h(OC_zF_{2z})_k-$ is the random copolymer and the compound wherein $-(OC_wF_{2w})_h(OC_zF_{2z})_k-$ is the alternating copolymer.

The compound represented by the formula (d) may be obtained by the following synthesis method. Firstly, a fluoroalkyl ether compound modified with a carboxylic acid is reacted with thionyl chloride to give a dicarboxylic acid chloride. Next, the dicarboxylic acid chloride is reacted with an alkanolamine that has an aliphatic hydrocarbon chain, to give an amide-modified fluoroalkylether compound. Next, this amide-modified fluoroalkylether compound is reduced with a catalyst such as LiAlH$_4$ (lithium aluminum hydride) to give the fluoroalkylether compound of the formula (d). NaBH$_4$ or Bu$_3$SnH can be used as the catalyst instead of LiAlH$_4$.

In the case where the compound represented by the formula (d) is used as a component of the lubricant of the present invention, the portion represented by $-(OC_mF_{2m})_p(OC_nF_{2n})_q-$ in the formula (a) may be preferably the same as the portion represented by $-(OC_wF_{2w})_h(OC_zF_{2z})_k-$ in the formula (d). In other words, it is preferable that "m"="w", "n"="z", "p"="h" and "q"="k." In that case, these two components have good mutual solubility since the basic skeletons of these two components become common. Similarly, in the case where the compound of the formula (a) and the compound of the formula (b) are combined with the compound of the formula (d), the portion represented by $-(OC_mF_{2m})_p(OC_nF_{2n})_q-$ in the formula (a), the portion represented by $-(OC_xF_{2x})_s(OC_yF_{2y})_t-$ in the formula (b) and the portion represented by $-(OC_wF_{2w})_h(OC_zF_{2z})_k-$ in the formula (d) may be preferably the same. In other words, it is preferable that "m"="x"="W", "n"="y"="z", "p"="s"="h" and "q"="t"="k." In that case, three components have good mutual solubility since the basic skeletons of three components become common.

In the case where the lubricant of the present invention includes a fluorine-based diester dicarboxylic acid compound represented by the formula (a), a fluorine-based diester compound represented by the formula (b) and/or a fluorine-based monoester compound represented by the formula (c), and a fluorine-based amino-alcohol compound represented by the formula (d), the mixing weight ratio of the compound of the formula (a) to the other two or three compounds (that is, (b)+(d) or (c)+(d) or (b)+(c)+(d)) may be preferably in a range of 1:9 to 9:1, more preferably in a range of 2:8 to 9:1 and still more preferably in a range of 4:6 to 9:1. In such a lubricant, the mixing weight ratio of the compound represented by the formula (b) and/or the compound represented by the formula (c) to the compound represented by the formula (d) may be preferably in a range of 1:9 to 9:1, more preferably in a range of 2:8 to 8:2, and still more preferably in a range of 4:6 to 6:4. In the case where the lubricant includes all the compounds represented by the formulae (b), (c) and (d), the mixing weight ratio may be preferably in a range of 1:1:18 to 9:9:2 ((b):(c):d)).

The lubricant of the present invention may further includes another lubricant, a corrosion inhibitor and/or an extreme-pressure agent in addition to the compounds represented by the formulae (a) to (d). In that case, the total amount of the compound of the formula (a) and the compound of the formula (b) and/or the compound of the formula (c) and the optionally added compound of the formula (d) may be preferably 30% by weight and more preferably 50% by weight of the total amount of the lubricant containing these compounds and another lubricant and so on. When the total amount of the compound of the formula (a) and the compound of the formula (b) and/or the compound of the formula (c) and the optionally added compound of the formula (d) is less than 30% by weight, such a composition may not confer good lubricating property to a magnetic recording medium whose lubricant layer is formed of the composition.

The magnetic recording medium of the present invention is a magnetic recording medium having a ferromagnetic metal film formed as a magnetic layer on a non-magnetic base, a protective film formed on the magnetic layer, and a lubricant layer formed on the protective film, wherein the lubricant layer includes the lubricant of the present invention. The amount of the lubricant of the present invention contained in the lubricant layer may be preferably in a range of 0.05 mg to 100 mg per 1 m$^2$ of a surface of the lubricant layer, and more preferably in a range of 0.1 mg to 50 mg per 1 m$^2$ of the surface. In order to distribute such a small amount of lubricant uniformly, the lubricant layer of the magnetic recording medium of the present invention may be preferably formed according to the following method.

The lubricant layer is formed on the protective film after the ferromagnetic metal film and the protective film have been formed on the non-magnetic base in this order using conventional materials and methods. The step of forming the lubricant layer includes the steps of preparing an application solution by dissolving the lubricant of the present invention into a mixed organic solvent of a hydrocarbon-based solvent and an alcohol-based solvent, and applying the application solution onto the protective film and then drying the applied application solution so as to evaporate the mixed organic solvent. The evaporation of the mixed organic solvent leaves the lubricant which has been dissolved in the solvent on the protective film so that the lubricant layer is formed. Therefore, even if the application solution is applied thickly, a very thin and uniform lubricant layer can be formed on the protective film as a result of the evaporation of the solvent. That is, a small amount of lubricant covers the protective film uniformly to form the lubricant layer.

The hydrocarbon-based solvents that can be used in the present invention include, for example, toluene, hexane, heptane, octane, nonane, xylene, and ketone. The alcohol-based solvents that can be used in the present invention include for example, a lower alcohol such as methyl alcohol, ethyl alcohol, propyl alcohol, isopropyl alcohol and butyl alcohol and so on. A preferable mixed organic solvent may be, for example, a mixed solvent of toluene and isopropyl alcohol, a mixed solvent of hexane and isopropyl alcohol or a mixed solvent of heptane and isopropyl alcohol. If the ratio of the alcohol-based solvent is too large, unevenness of application is liable to be generated, whereas if the ratio of the hydrocarbon-based solvent is too large, it is uneconomical. Accordingly, the two solvents are mixed for use preferably at a mixing ratio within a range of 1:9 to 9:1 by weight, and more preferably 3:7 to 7:3 by weight.

The concentration of the application solution and the application thickness are adjusted so that the lubricant layer formed on the protective film after the evaporation of the solvent may have a desired thickness. Typically, it is preferable that the application solution having a lubricant concentration of 100 ppm to 10000 ppm is applied to have a thickness of 1 µm to 50 µm.

The method of applying the application solution may be any of wet application methods such as a bar coating method, a gravure coating method, a reverse roll coating method, a die coating method, a dipping method, or a spin-coating method, or a vacuum vapor deposition method.

After the application solution is applied, a drying process is carried out to evaporate the mixed organic solvent, whereby the lubricant layer is formed on the protective film. The drying process can be performed either by heating or by natural drying. A preferable thickness of the lubricant layer depends on the lubricant composition. A preferable thickness of the lubricant layer may be typically 3 nm to 5 nm, but not the thickness is not limited thereto.

By using this mixed organic solvent, it is possible to obtain a lubricant layer having a uniform thickness without application unevenness, and also it is possible to form a lubricant layer having an extremely small thickness of several nanometers after the solvent is finally evaporated. As a result, a magnetic recording medium having an excellent lubricating property and a high practical reliability is obtained.

As described above, the magnetic recording medium of the present invention may be produced using conventional materials and conventional procedures except for the lubricant layer.

For example, the non-magnetic base may be, for example, a film made of polyethylene terephthalate, polyethylene naphthalate, aromatic polyamide, or aromatic polyimide, a film made of a vinyl-based resin such as polyvinyl chloride or polyvinylidene chloride; a substrate made of polycarbonate, glass, ceramic, carbon, a metal such as aluminum or copper, a light metal such as an aluminum alloy or a titanium alloy, or a monocrystal silicon; or paper. When a substrate whose stiffness is high (such as a substrate made of an aluminum alloy and a glass substrate) is used as the non-magnetic base, its surface may be hardened by forming an oxide film or a Ni—P film on the substrate surface by, for example, an alumite treatment.

In view of compatibility between practical reliability and good RF output, it is preferable that a process of forming protrusions having a diameter of 20 nm to 700 nm and a height of 5 nm to 70 nm is performed on a surface of the non-magnetic base where the ferromagnetic metal film is formed, that is, the surface which contacts the magnetic layer directly or through a base layer if any. The protrusions may be formed by dispersing and fixing, on the surface, ultrafine particles made of an inorganic material such as $SiO_2$ or ZnO or ultra fine particles made of an organic material such as an imide. Alternatively, the protrusions may be formed by forming a polymeric material containing such particles into a film.

In the magnetic recording medium of the present invention, the magnetic layer is the ferromagnetic metal film. The ferromagnetic metals suitable for the magnetic layer include Fe-based metal, Co-based metal and Ni-based metal. Herein, the "Co-based metal" means cobalt or an alloy containing a cobalt as a main component, preferably in an amount of 50% by atom. This is applicable to "Fe-based metal" and "Ni-based metal."

Specifically, the ferromagnetic metal film may be formed of one or more materials selected from Fe, Co, Ni and alloy such as Co—Ni, Co—Fe, Co—Cr, Co—Cu, Co—Pt, Co—Pd, Co—Sn, Co—Au, Fe—Cr, Fe—Co—Ni, Fe—Cu, Ni—Cr, Fe—Co—Cr, Co—Ni—Cr, Co—Pt—Cr and Fe—Co—Ni—Cr. The ferromagnetic metal film may contain oxygen, and the oxygen may be contained in the form of an oxide of the metal or the alloy. The ferromagnetic metal may be in the form of monolayer-film or multilayer-film.

The ferromagnetic metal film may be formed by an ionplating method, a sputtering method, or an electron beam vapor deposition. In the case where the ferromagnetic metal film is formed under an oxygen atmosphere, the ferromagnetic metal film contains oxygen. The thickness of the ferromagnetic metal film may be generally in a range of 30 nm to 300 nm.

The protective film may be preferably a carbon film. The carbon film has a high Vickers hardness of about $2.54 \times 10^4$ N/$mm^2$ (2500 kg/$mm^2$), and prevents damages to the magnetic tape together with the lubricant layer. In consideration of the balance between practical reliability and output, the thickness thereof is preferably in a range of 1 nm to 20 nm.

The carbon film may be preferably graphite-like carbon or diamond-like carbon. The diamond-like carbon is most preferable material since it has an appropriate hardness and suppresses damage of the magnetic recording medium without damaging the magnetic head. The carbon film made of the graphite-like carbon or the diamond-like carbon may be formed by a plasma CVD method using a hydrocarbon gas alone or a mixed gas of the hydrocarbon gas and an inert gas. Alternatively, the film can be formed by a sputtering method using a carbon target.

Specifically, the hydrocarbon gas or the mixed gas of the hydrocarbon gas and the inert gas such as argon is introduced into a vacuum container, and electric discharge is generated in the inside of the vacuum container while maintaining the pressure in the container to be 0.13 Pa to 130 Pa, thereby to generate plasma of the hydrocarbon gas to form the carbon film on the ferromagnetic metal film. The electric discharge may be generated by using either of the external electrode system and the internal electrode system. The electric discharge frequency can be experimentally determined. Further, by applying a voltage of 0 KV to −3 KV to an electrode disposed on the non-magnetic base side, the hardness of the carbon film can be increased and the adhesion between the carbon film and the ferromagnetic metal film can be improved. Methane, ethane, propane, butane, pentane, hexane, heptane, octane, benzene, or the like, for example, may be used as the hydrocarbon gas.

Here, in order to form the hard carbon film, it is desirable to increase the electric discharge energy and also it is desirable to maintain the temperature of the non-magnetic base to be high. For example, it is desirable that the electric discharge energy has an effective value of not less than 600V by superposing an AC current such as a high frequency current and a DC current.

In the present invention, it is desirable that the carbon film has a nitrogen-containing plasma polymerized film on a top surface portion thereof and the lubricant layer is formed on the nitrogen-containing plasma polymerized film of the carbon film. By nitrogen-containing plasma polymerization, i.e. by forming a nitrogen-containing plasma polymerized film on a carbon film, an amino group is present on the top surface portion of the carbon film, whereby the adhesion strength between the lubricant layer and the carbon film further increases and the durability of the magnetic recording medium is further improved. In addition to this, since the lubricant layer comprises specific fluorine-containing compounds, it is possible to obtain a magnetic recording medium having high practical reliability and excellent lubricating property with improved running durability, still durability and corrosion resistance without deteriorating the electromagnetic conversion characteristics.

The nitrogen-containing plasma polymerized film is formed, for example, by introducing a gasified amine compound such as propylamine, butylamine, ethylenediamine, propylenediamine or tetramethylenediamine into a vacuum container and generating a high frequency electric discharge in the vacuum container while maintaining the pressure within the container to be 0.13 Pa to 130 Pa. The nitrogen-containing plasma polymerized film improves the chemical adsorptivity of the lubricant containing the specific compounds as described, which results in a higher adherence strength between the lubricant layer and the carbon film. A suitable thickness of the nitrogen-containing plasma polymerized film is less than 3 nm. If the nitrogen-containing plasma polymerized film has a larger thickness than this, the carbon film decreases its protective effect. The method of forming a nitrogen-containing plasma polymerized film on a top surface portion of the carbon film is disclosed in U.S. Pat. Nos. 5,540,957 and 5,637,393, the disclosures of which are incorporated herein by reference.

The magnetic recording medium of the present invention may have a back coat layer on a surface of the non-magnetic base which surface is opposite to the surface where the magnetic layer is formed. The back coat layer may be a layer formed of one or more materials selected from polyurethane, nitrocellulose, polyester, carbon, calcium carbonate, and the like, or may be a thin film of a metal or a metal oxide. The thickness of the back coat layer may be preferably in a range of about 50 nm to about 500 nm.

The construction of the magnetic recording medium of the present invention is not limited to the above construction. For example, the magnetic recording medium of the present invention may have a construction wherein a reinforcing layer is formed by vapor deposition of a metal on the surface of the non-magnetic base which is opposite to the surface where the magnetic layer is formed, and the back coat layer is formed on the reinforcing layer. Alternatively, the magnetic recording medium of the present invention may have a construction wherein the reinforcing layer is formed on a surface of the non-magnetic base where protrusions are formed and the magnetic layer is formed on the reinforcing layer, or a construction wherein a base layer and the magnetic layer are formed on the reinforcing layer in this order. The magnetic recording medium of the present invention may be any of a tape medium and a disk medium.

In FIG. 1, a magnetic recording medium (100) according to one embodiment of the present invention is schematically shown in section. In FIG. 1, a magnetic layer (2) is formed on one of surfaces of a non-magnetic base (1), a protective film (3) is formed on the magnetic layer, and a lubricant layer (4) is formed on the protective film (3), whereas a back coat layer (5) is formed on the other surface of the non-magnetic base (1).

EXAMPLES

Hereafter, the present invention will be explained in detail by examples, but it goes without saying that the present invention is not limited by these examples.

Example 1

A magnetic recording medium of the present invention and a method for producing the magnetic recording medium are described as Example 1. As a non-magnetic base, a polyethylene terephthalate film which had protrusions on a surface was prepared. Specifically, a polyethylene terephthalate film which had (1) gently inclined protrusions (having an average height of 4 nm and a diameter of 1 μm) at a density of several counts per 100 μm$^2$, and (2) steep protrusions having a diameter of 15 nm at a density of $1 \times 10^7$ counts per 1 mm$^2$ was used. The gently inclined protrusions were formed by forming a polymeric material containing silica ultrafine particles into a film. The steep protrusions were formed by fixing silica colloid particles having a diameter of 15 nm on the surface of the polyethylene terephthalate film using an ultraviolet curable epoxy resin. The polyethylene terephthalate film used in this example had few protrusions having a relatively large size which were formed on its surface by fine particles that resulted from residue of a polymerization catalyst.

A ferromagnetic metal film of cobalt (Co) was formed on the film surface having the protrusions by a continuous obliquely vacuum vapor deposition method in the presence of oxygen in minutes amounts. The film thickness was 100 nm. The oxygen content in the ferromagnetic metal film was 5% by atomic fraction.

Next, a protective film of diamond-like carbon was formed on the ferromagnetic metal film by a plasma CVD method. The film thickness was 5 nm. The protective film was formed by introducing a gas obtained by mixing a hexane gas and an argon gas at a ratio of 4:1 (pressure ratio) into a vacuum container, and applying an electric current obtained by superposing an AC current having a frequency of 20 KHz and a voltage of 1500 V on a DC current of 1000 V, to an electrode in an electric discharge tube while maintaining the total gas pressure to be 39 Pa. Further, a propylamine gas was introduced on the carbon film and a high frequency plasma process of 10 KHz was performed while maintaining a pressure of 6.5 Pa, to form a nitrogen-containing plasma polymerized film having a thickness of 2.5 nm on a top surface portion of the carbon film.

Next, a lubricant was prepared by mixing a fluorine-based diester dicarboxylic acid compound represented by a formula (a1) and a fluorine-based monoester compound represented by a formula (c1) at a weight ratio of 1:1. This lubricant was dissolved into a mixed organic solvent obtained by mixing isopropyl alcohol and toluene at a weight ratio of 1:1 so that an application solution was obtained. The concentration of the lubricant was 1000 ppm.

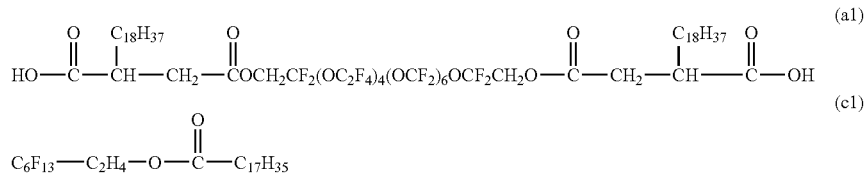

(a1)

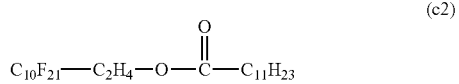

(c1)

This application solution was applied into a 50 μm thickness on the protective film by the wet application method using a reverse roll coater. Subsequently, the solvent was evaporated by a drying treatment. In the end, a lubricant layer wherein the lubricant was contained in an amount of 7 mg per 1 m² was formed on the protective film. A tape material produced as shown above was cut by a slitter into an 12.7 mm (½ inch) width to obtain a magnetic tape sample.

Example 2

A lubricant was prepared by mixing the fluorine-based diester dicarboxylic acid compound represented by a formula (a1) and a fluorine-based monoester compound represented by a formula (c2) at a weight ratio of 1:1. A magnetic tape sample was produced in the same manner as in Example 1 using this lubricant.

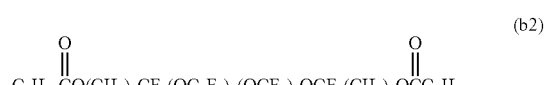

(c2)

Example 3

A lubricant was prepared by mixing a fluorine-based diester dicarboxylic acid compound represented by a formula (a2) and a fluorine-based diester compound represented by a formula (b1) at a weight ratio of 1:1. A magnetic tape sample was produced in the same manner as in Example 1 using this lubricant.

Example 4

A lubricant was prepared by mixing the fluorine-based diester dicarboxylic acid compound represented by the formula (a1) and the fluorine-based diester compound represented by the formula (b1) at a weight ratio of 7:3. A magnetic tape sample was produced in the same manner as in Example 1 using this lubricant.

Example 5

A lubricant was prepared by mixing the fluorine-based diester dicarboxylic acid compound represented by the formula (a1) and a fluorine-based diester compound represented by a formula (b2) at a weight ratio of 4:6. A magnetic tape sample was produced in the same manner as in Example 1 using this lubricant.

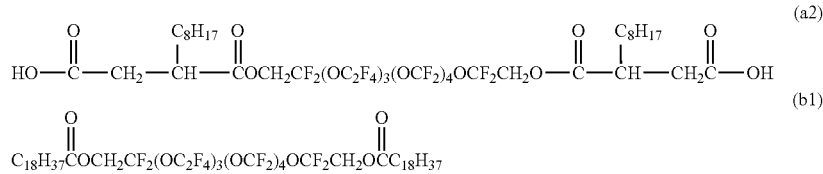

(b2)

Example 6

A lubricant was prepared by mixing a fluorine-based diester dicarboxylic acid compound represented by a formula (a3) and the fluorine-based diester compound represented by the formula (b2) at a weight ratio of 1:1. A magnetic tape sample was produced in the same manner as in Example 1 using this lubricant.

(a2)

(b1)

(a3)

Example 7

A lubricant was prepared by mixing the fluorine-based diester dicarboxylic acid compound represented by the formula (a3) and a fluorine-based diester compound represented by a formula (b3) at a weight ratio of 1:1. A magnetic tape sample was produced in the same manner as in Example 1 using this lubricant.

(b3)
$$C_8H_{17}CH=CHC_7H_{14}COCH_2CF_2(OC_2F_4)_3(OCF_2)_4OCF_2CH_2OCC_7H_{14}CH=CHC_8H_{17}$$

Example 8

A lubricant was prepared by mixing the fluorine-based diester dicarboxylic acid compound represented by the formula (a1), the fluorine-based diester compound represented by the formula (b1) and the fluorine-based monoester compound represented by the formula (c1) at a weight ratio of 1:1:1. A magnetic tape sample was produced in the same manner as in Example 1 using this lubricant.

Example 9

A lubricant was prepared by mixing the fluorine-based diester dicarboxylic acid compound represented by the formula (a1), the fluorine-based diester compound represented by the formula (b1) and a fluorine-based amino alcohol compound represented by a formula (d1) at a weight ratio of 1:1:1. A magnetic tape sample was produced in the same manner as in Example 1 using this lubricant.

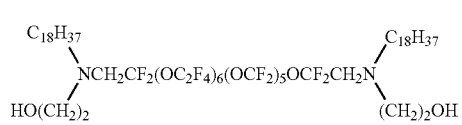

(d1)

Example 10

A lubricant was prepared by mixing the fluorine-based diester dicarboxylic acid compound represented by the formula (a1), the fluorine-based monoester compound represented by the formula (c1) and the fluorine-based amino alcohol compound represented by a formula (d1) at a weight ratio of 1:1:1. A magnetic tape sample was produced in the same manner as in Example 1 using this lubricant.

Example 11

A lubricant was prepared by mixing the fluorine-based diester dicarboxylic acid compound represented by the formula (a1), the fluorine-based diester compound represented by the formula (b1), the fluorine-based monoester compound represented by the formula (c1) and the fluorine-based amino alcohol compound represented by a formula (d1) at a weight ratio of 1:1:1:1. A magnetic tape sample was produced in the same manner as in Example 1 using this lubricant.

Comparative Example 1

The fluorine-based diester dicarboxylic acid compound represented by the formula (a1) was used alone as a lubricant and a magnetic tape sample was produced in the same manner as in Example 1.

Comparative Example 2

The fluorine-based diester compound represented by the formula (b1) was used alone as a lubricant and a magnetic tape sample was produced in the same manner as in Example 1.

Comparative Example 3

A known compound represented by a formula (e1) was used alone as a lubricant and a magnetic tape sample was produced in the same manner as in Example 1.

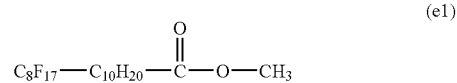

(e1)

Comparative Example 4

The fluorine-based amino alcohol compound represented by the formula (d1) was used alone as a lubricant and a magnetic tape sample was produced in the same manner as in Example 1.

Comparative Example 5

A known lubricant represented by a formula (z1) was used alone as a lubricant and a magnetic tape sample was produced in the same manner as in Example 1.

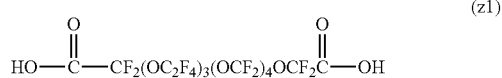

(z1)

Comparative Example 6

A lubricant was prepared by mixing the fluorine-based diester dicarboxylic acid compound represented by the formula (a1) and the fluorine-based monoester compound represented by the formula (e1) at a weight ratio of 1:1. A magnetic tape sample was produced in the same manner as in Example 1 using this lubricant.

Comparative Example 7

The fluorine-based monoester compound represented by the formula (c1) was used alone as a lubricant and a magnetic tape sample was produced in the same manner as in Example 1.

Comparative Example 8

A lubricant was prepared by mixing the fluorine-based diester dicarboxylic acid compound represented by the formula (a2) and the fluorine-based diester compound represented by the formula (b1) at a weight ratio of 1:1. A magnetic tape sample was produced in the same manner as in Example 1 except for preparing an application solution by dissolving this lubricant into isopropyl alcohol (a single solvent).

Comparative Example 9

A lubricant was prepared by mixing the fluorine-based diester dicarboxylic acid compound represented by the formula (a2) and the fluorine-based diester compound represented by the formula (b1) at a weight ratio of 1:1. A magnetic tape sample was produced in the same manner as in Example 1 except for preparing an application solution by dissolving this lubricant into toluene (a single solvent).

With respect to each of the magnetic tape samples obtained in Examples 1 to 11 and Comparative Examples 1 to 9, the following evaluation tests were conducted.

(1) Running Test

Each sample was wrapped, at a wrapped angle of 90°, around a friction member which was made of stainless (SUS420J2; a surface roughness 0.2 S) and had an outer diameter of 0.6 mm, and wound off at a speed of 18 mm/sec applying a tension of 2N and wound up at the same speed and the tension was measured on the wound-up side. Environmental conditions were 23° C. and 50% relative humidity. A coefficient of dynamic friction was calculated according to the Euler's formula based on a ratio of the tension of the wound-off side to the tension of the wound-up side. A set of one wound-off and one wound-up was counted as one pass, and the coefficient of dynamic friction was measured at 100th pass and 1000th pass.

(2) Short-Shuttle Test

The short-shuttle test was conducted under an environment of 3° C. and 5% relative humidity using a data storage tape drive S-AIT which was available under the trade name "SAITE1300-S" from Sony Corporation. The drive was altered for this test. The short-shuttle test was carried out by repeatedly running a portion (herein, 4 m length) of the entire tape and determining the repeated pass cycles until fail-out. The results were shown by the repeated pass cycles (the number of repeated running) when the fail-out occurred. As the pass cycles are higher, a tape is less liable to be damaged even if the running is repeated, and therefore the durability is evaluated higher.

(3) Durability Test

The durability was evaluated by the repeatedly reproducible cycles of a sample until the head clogging occurred. A data storage tape drive S-AIT which was available under the trade name "SAITE1300-S" from Sony Corporation was altered for measuring RF (Radio Frequency) outputs. Using this altered drive, signals recorded on each sample were repeatedly reproduced and the head clogging was detected from error rates during the reproduction. Specifically, when the error rates was equal to or greater than $1\times10^2$ during the repeated reproduction, the head clogging was deemed to come up. Accordingly, the repeated pass cycles were measured until the occurrence of the head clogging. As the repeated pass cycles are higher, the durability is evaluated higher.

(4) Adsorptivity Test

Adsorptivity test was conducted by washing a sample having a lubricant layer with a solvent that was used for preparing the application solution for forming the lubricant layer and determining the residual ratio of the lubricant after this washing. The washing was carried out by immersing the sample in the solvent for 10 seconds. In this test, as the residual ratio is larger, the adroptivity is evaluated higher. The residual ratio of the lubricant was determined by detecting fluorine atoms by the ESCA analysis, and calculating from the variation in abundance of fluorine atoms between before and after the solvent washing.

The results of each test are shown in Table 1.

TABLE 1

| | Running Durability (Coefficient of Dynamic Friction) | | Short-Shuttle Test | Durability | Resicual Ratio of Lubricant (%) |
|---|---|---|---|---|---|
| | 100th pass | 1000th pass | (Pass Cycles) | (Pass Cycles) | |
| Example 1 | 0.20 | 0.22 | 5000 | 10000 | 65 |
| Example 2 | 0.20 | 0.22 | 5000 | 10000 | 63 |
| Example 3 | 0.22 | 0.24 | 3000 | 10000 | 68 |
| Example 4 | 0.21 | 0.23 | 3000 | 10000 | 69 |
| Example 5 | 0.23 | 0.26 | 3000 | 10000 | 68 |
| Example 6 | 0.22 | 0.23 | 3000 | 10000 | 70 |
| Example 7 | 0.22 | 0.24 | 3000 | 10000 | 67 |
| Example 8 | 0.20 | 0.22 | 4000 | 10000 | 79 |
| Example 9 | 0.21 | 0.22 | 4000 | 10000 | 81 |
| Example 10 | 0.21 | 0.22 | 4000 | 10000 | 80 |
| Example 11 | 0.20 | 0.21 | 5000 | 10000 | 80 |
| Comparative Example 1 | 0.22 | 0.26 | 1000 | 3000 | 72 |
| Comparative Example 2 | 0.34 | 0.44 | 500 | 3000 | 50 |
| Comparative Example 3 | 0.29 | 0.38 | 500 | 1000 | 48 |
| Comparative Example 4 | 0.23 | 0.25 | 1000 | 3000 | 72 |
| Comparative Example 5 | 0.16 | 0.22 | 500 | 1000 | 66 |
| Comparative Example 6 | 0.26 | 0.28 | 500 | 1000 | 58 |
| Comparative Example 7 | 0.24 | 0.31 | 500 | 3000 | 47 |
| Comparative Example 8 | 0.28 | 0.35 | 500 | 3000 | 71 |
| Comparative Example 9 | 0.29 | 0.36 | 500 | 1000 | 69 |

As will be apparent from the above Table 1, the samples obtained in Examples 1 to 11 wherein a combination of a specific fluorine-based dicarboxylic acid diester compound and a specific fluorine-based diester compound or a specific fluorine-based monoester compound was used as a lubricant, exhibited excellent running durability and durability under an environment of a normal temperature and a normal humidity and an environment of a low temperature and a low humidity. Specifically, a low coefficient of dynamic friction after 1000-pass running was maintained and the pass cycles determined in the short-shuttle test was over 3000 cycles, for each of the magnetic tapes obtained in Examples 1 to 11. The magnetic tapes of Comparative Examples 1, 2, 7 and 4 which were produced using only one of the compounds represented by the formulae (a), (b), (c) and (d) were inferior in runnability and durability. Also the magnetic tapes of Comparative Examples 3 and 5 which were produced using the known lubricants were inferior in runnability and durability. The magnetic tape of Comparative Example 6 which was produced using a mixture of the compound of the formula (a) and an ester other than the esters represented by the formulae (b) and (c) was inferior in runnability and durability compared to the samples of Examples 1 to 11. These results show that a first combination of the compound of the formula (a) and the compound of the formula (b) and/or the compound of the formula (c), and a second combination of the first combination and the compound of the formula (d) function as a lubricant for a magnetic recording medium very well. Particularly the magnetic tapes wherein the lubricant layers contain the compound (d) have a high residual ratio of lubricant (see Examples 9 to 11). This shows that the second combination is superior in adsorptivity. Although the combination of the compound of the formula (a) and the compound of the formula (c) shows a slightly low residual ratio of lubricant (see Examples 1 and 2), the pass cycles in the short-shuttle test are high, which shows that this combination has good durability. Further, the results of Example 3 and Comparative Examples 8 and 9 show that the lubricant layer having good characteristics can be formed by dissolving the lubricant of the present invention into a mixed solvent of a hydrocarbon-based solvent and an alcohol-based solvent and applying the solution.

CROSS-REFERENCE TO RELATED APPLICATIONS

The present application claims a priority under 35 U.S.C. §119 to Japanese Patent Application Nos. 2004-141960 filed on May 12, 2004, entitled "LUBRICANT, MAGNETIC RECORDING MEDIUM AND PRODUCTION METHOD OF MAGNETIC RECORDING MEDIUM" and 2005-47435 filed on Feb. 23, 2005 entitled "LUBRICANT, MAGNETIC RECORDING MEDIUM AND PRODUCTION METHOD OF MAGNETIC RECORDING MEDIUM." The contents of those applications are incorporated herein by the reference thereto in their entirety.

What is claimed is:

1. A lubricant comprising at least one compound selected from fluorine-based diester dicarboxylic acid compounds represented by a formula (a), and at least one compound selected from fluorine-based diester compounds represented by a formula (b) and fluorine-based monoester compounds represented by a formula (c):

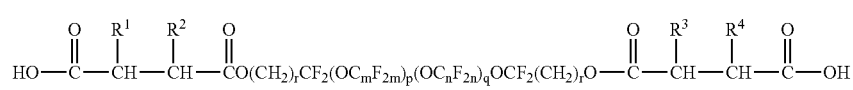

wherein, $R^1$, $R^2$, $R^3$ and $R^4$ each represent hydrogen, an aliphatic alkyl group or an aliphatic alkenyl group, at least one of $R^1$ and $R^2$ is hydrogen, at least one of $R^3$ and R4 is hydrogen, "m" is an integer of 1 to 6, "n" is an integer of 1 to 5, "p" and "q" each are an integer of 0 to 30 and "r" is an integer of 1 to 12;

wherein, $R^5$ and $R^6$ each represent an aliphatic alkyl group or an aliphatic alkenyl group, "x" is an integer of 1 to 6, "y" is an integer of 1 to 5, "s" and "t" each are an integer of 0 to 30 and "u" is an integer of 1 to 12;

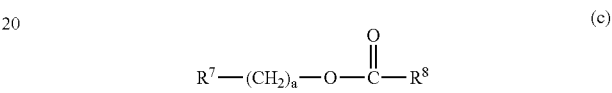

wherein, $R^7$ represents a fluoroalkyl group, a fluoroalkenyl group, a fluoroether group or a fluoropolyether group, $R^8$ represents an aliphatic alkyl group or an aliphatic alkenyl group, and "a" is an integer of 1 to 12.

2. The lubricant according to claim 1, which comprises at least one compound selected from the fluorine-based diester dicarboxylic acid compounds represented by the formula (a), and at least one compound selected from the fluorine-based diester compounds represented by the formula (b).

3. The lubricant according to claim 1, which comprises at least one compound selected from the fluorine-based diester dicarboxylic acid compounds represented by the formula (a), and at least one compound selected from the fluorine-based monoester compounds represented by the formula (c).

4. The lubricant according to claim 1, wherein a mixing ratio of the fluorine-based diester dicarboxylic acid compounds represented by the formula (a) to the fluorine-based diester compounds represented by the formula (b) and/or the fluorine-based monoester compounds represented by the formula (c) is within a range of 1:9 to 1:9 by weight.

5. The lubricant according to claim 1, which further comprises a fluorine-based amino-alcohol represented by a formula (d):

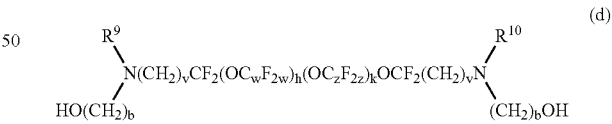

wherein $R^9$ and $R^{10}$ each represent hydrogen, an aliphatic alkyl group or an aliphatic alkenyl group, "b" is an integer of 1 to 12, "v" is an integer of 1 to 12, "w" is an integer of 1 to 6, "z" is an integer of 1 to 5, and "h" and "k" each are an integer of 0 to 30.

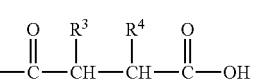

6. The lubricant according to claim 5, wherein a mixing ratio of the fluorine-based diester dicarboxylic acid compounds represented by the formula (a) to the fluorine-based diester compounds represented by the formula (b) and/or the fluorine-based monoester compounds represented by the formula (c) and the fluorine-based amino-alcohol represented by the formula (d) is within a range of 1:9 to 1:9 by weight.

7. The lubricant according to claim 6, wherein a mixing ratio of the fluorine-based diester compounds represented by the formula (b) and/or the fluorine-based monoester compounds represented by the formula (c) to the fluorine-based amino-alcohol compound is within a range of 1:9 to 9:1 by weight.

8. A lubricant for a magnetic recording medium, which comprises the lubricant according to claim 1.

9. A magnetic recording medium comprising a ferromagnetic metal film formed as a magnetic layer on a non-magnetic base, a protective film formed on the magnetic layer and a lubricant layer formed on the protective film, wherein the lubricant layer includes at least one lubricant according to claim 1.

10. The magnetic recording medium according to claim 9, wherein the protective film is of diamond-like carbon.

11. The magnetic recording medium according to claim 9, wherein the protective film is a carbon film which comprises a nitrogen-containing plasma polymerized film on a top surface portion thereof and the lubricant layer is formed on the nitrogen-containing plasma polymerized film of the carbon film.

* * * * *